United States Patent [19]
Lundahl

[11] Patent Number: 5,303,324
[45] Date of Patent: Apr. 12, 1994

[54] METHOD AND APPARATUS FOR PROVIDING CONTROLLED LIGHT DISTRIBUTION FROM A CYLINDRICAL FIBEROPTIC DIFFUSER

[75] Inventor: Scott Lundahl, Ridgewood, N.J.

[73] Assignee: American Cyanamid Company, Wayne, N.J.

[21] Appl. No.: 968,140

[22] Filed: Oct. 29, 1992

[51] Int. Cl.⁵ .............................. G02B 6/00
[52] U.S. Cl. ....................... 385/147; 385/34; 385/901; 606/2; 606/7
[58] Field of Search ............ 385/31, 34, 146, 147, 385/900, 901; 359/599, 837; 606/2, 7

[56] References Cited

U.S. PATENT DOCUMENTS

| | | |
|---|---|---|
| 4,459,642 | 7/1984 | Mori ............................ 385/139 X |
| 4,660,925 | 4/1987 | McCaughan, Jr. ............ 350/96.15 |
| 4,770,488 | 9/1988 | Shank et al. ................. 385/79 |
| 4,824,195 | 4/1989 | Khoe ........................... 350/96.18 |
| 4,889,129 | 12/1989 | Dougherty et al. ........... 128/664 |
| 5,074,632 | 12/1991 | Potter .......................... 385/31 |
| 5,151,096 | 9/1992 | Khoury ........................ 606/7 |
| 5,196,005 | 3/1993 | Doiron et al. ................ 606/7 |

Primary Examiner—Rodney B. Bovernick
Assistant Examiner—Stephen W. Barns
Attorney, Agent, or Firm—K. J. Dow

[57] ABSTRACT

The invention discloses a cylindrical optical radiating device for obtaining controlled light distribution in a cylindrical pattern from an optical fiber. The device is constructed of a solid cylindrical tip made from material containing an optical scattering material in which a tapered central lumen having a conical shape has been drilled, cast or bored. Light emerging from the end of the fiber is radiated out in a cylindrical pattern through the use of the tapered central lumen.

10 Claims, 4 Drawing Sheets

METHOD AND APPARATUS FOR PROVIDING CONTROLLED LIGHT DISTRIBUTION FROM A CYLINDRICAL FIBEROPTIC DIFFUSER

BACKGROUND OF THE INVENTION

1. Field of the Invention

The invention relates to fiber-optic diffusers for use in the photodynamic therapy or diagnosis of cancer and related conditions in a patient. The invention provides a method and apparatus for controlling the output distribution of a cylindrical fiber-optic diffuser.

2. Description of the Related Art

"Photodynamic Therapy", (PDT) is a well known method of treating tumors and other diseases in humans in which a photosensitizing substance is administered to a patient and allowed to concentrate preferentially in tumor tissue and then light, at an appropriate wavelength, is used to illuminate the tumor tissue. The light activates a chemical reaction with the substance in the tumor tissue and destroys the cancer cells. Reference is made to U.S. Pat. No. 4,889,129 for a discussion of the particulars of one such PDT method and apparatus for practicing the method.

Since the photoactivation of the photosensitizer in tissue through the absorption of light energy is the primary event leading to photodynamic destruction of tissue, it is critical to deliver the light in a targeted manner to the tumor tissue at an optimum "dose" which is matched to the target tissue volume. This is accomplished through the use of fiber optic delivery systems to target the light at appropriate wavelengths to the tumor tissue to be treated. For tubular body areas such as a bronchus or esophagus, it is common to use a fiber optic diffuser which delivers the light in a cylindrical scattering pattern. Thus, for PDT treatment of esophogeal cancer, an optical fiber is required to be equipped with an apparatus at the tip which disperses light propagating along the fiber in a uniform cylindrical pattern with respect to the central axis of the optical fiber.

U.S. Pat. No. 4,660,925 describes a fiber optic cylindrical diffuser which is constructed of an optical fiber with an exposed core at one end, and a scattering medium surrounding the exposed core constructed to produce the desired uniform cylindrical pattern. The exposed core coated with the scattering medium is then inserted into an open-ended tube and the interstices between the scattering medium and the tubes are then filled with additional scattering medium.

U.S. Pat. No. 5,074,632 discloses an improvement on this method of preparing a cylindrical diffuser which includes an optical fiber with an exposed core tip, a thin layer of scattering medium coated on the exposed tip, and a sleeve member enclosing the tip without touching the scattering medium and fixed on the jacket of the fiber. Both of these devices rely on the diffusing coatings which must be manually applied to the fiber at the time of manufacture to convert the forward moving light stream in the fiber optic into a radially emitting cylindrical light stream.

Another approach to producing approximately uniform cylindrical patterns of light has been taken by Quentron optics Pty. Ltd. of Adelaide, Australia discussed in U.S. Pat. No. 4,660,925. The Quentron fibers utilize a fiber optic core which is tapered to a point at its tip, allowing the light to escape at each point along the tapered core. However, the need to taper the core of the optical fiber at its tip is a time consuming and costly procedure.

In using such cylindrical diffusers for photodynamic therapy, it is essential that the light distribution from the fiber optic be as uniform as possible within a volume of tissue containing a tumor, so the light can be delivered at an appropriate and consistent dosage level. The apparatus must be capable of delivering the light for effective treatment without developing "hot spots" or mechanical or optical failures during use. In addition, the device must be capable of providing consistent output reproducibility. Ideally, the device should be easily modified to provide different output distribution profiles for different applications.

SUMMARY OF THE INVENTION

The invention discloses a cylindrical optical radiating device for obtaining controlled light distribution in a cylindrical pattern from a diffusing fiber. The device is constructed of a solid cylindrical body made from material containing an optical scattering medium in which tapered central lumen has been drilled, cast or bored. An optical fiber is inserted into the open end of the tapered bore in a manner such that it is held coaxially with the center of the bore. Light emerging from the end of the fiber diverges from the central axis because of the index of refraction between the optical fiber and the medium inside the tapered bore and are diffused outward. Upon striking the inside of the tapered bore and the cylindrical body containing the scattering material, the light is diffused radially in a cylindrical pattern. Through the use of the tapered bore, it is possible to obtain an output distribution which is radially and linearly uniform even though the energy distribution is not uniform within the core of the fiber optic.

The tapered bore in the cylindrical diffuser of the present invention makes use of multiple optical interfaces, as opposed to a single optical interface, which improves the ability of the device to convert the forward moving light stream into a radially emitting light stream leading to improved output pattern reproducibility.

Rather than using a diffusing coating which must be manually applied to each fiber at the time of manufacture, the present invention utilizes a single component diffuser which may be machine produced thus providing a substantial improvement in both ease of manufacture and output pattern reproducibility.

DETAILED DESCRIPTION

Figure 1:
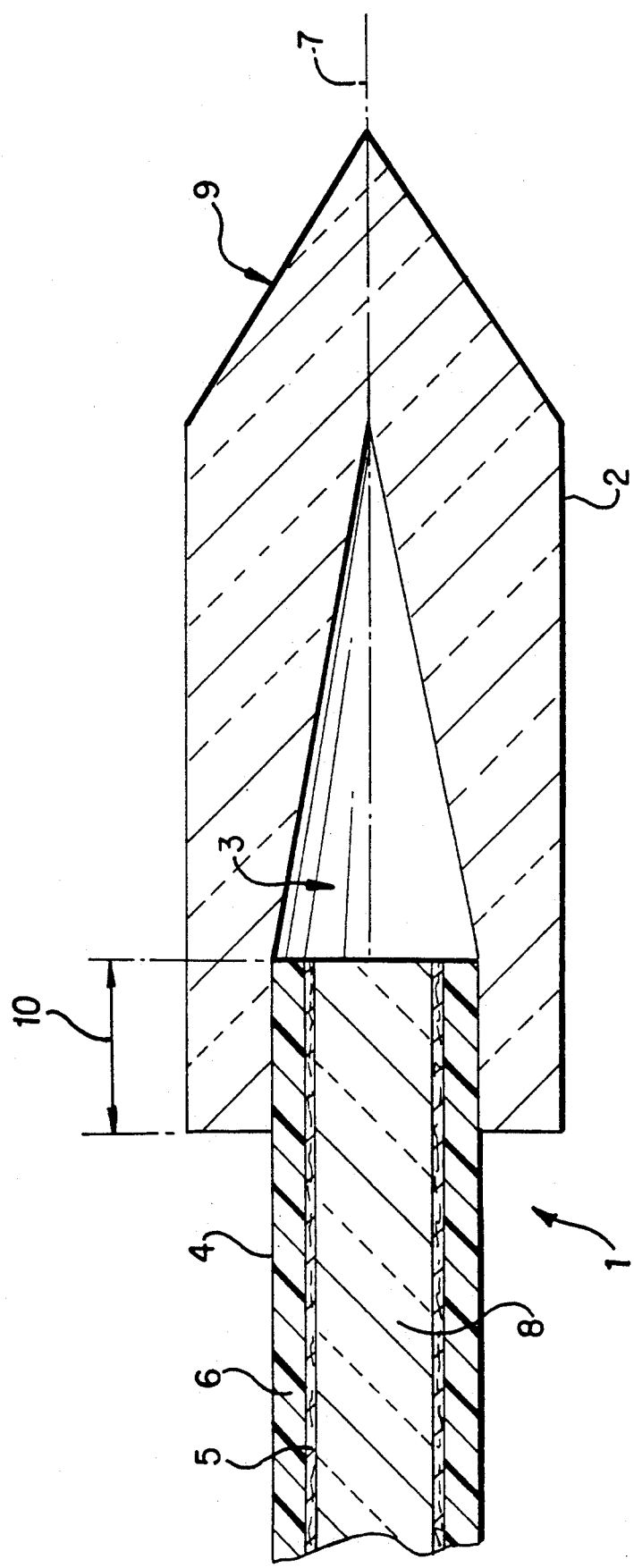
FIG. 1 is a cross sectional view of a fiber optic cylindrical diffuser of the invention.

Referring to the drawings with greater particularity, there is shown in FIG. 1 a fiber optic cylindrical diffuser 1. The cylindrical diffuser 1 is constructed of a solid cylindrical tip 2 made from material containing an optical scattering media. A tapered central lumen 3 is longitudinally drilled, cast or bored in the center of the cylindrical tip 2 such that the tapered central lumen 3 has a conical shape culminating at a point adjacent to the end of the solid cylindrical tip 2. An optical fiber 4 is inserted into the large end of the tapered central lumen 3 in a manner such that it is held coaxially with the center line 7 of the lumen 3. The cylindrical body 2 is fixed on the jacket of the fiber which consists of a cladding 5 and a sheathing 6. The tapered central lumen 3 may be filled with air or other filler which has an index of refraction which is less than or equal to that of the glass of the optical fiber 4.

Figure 2:
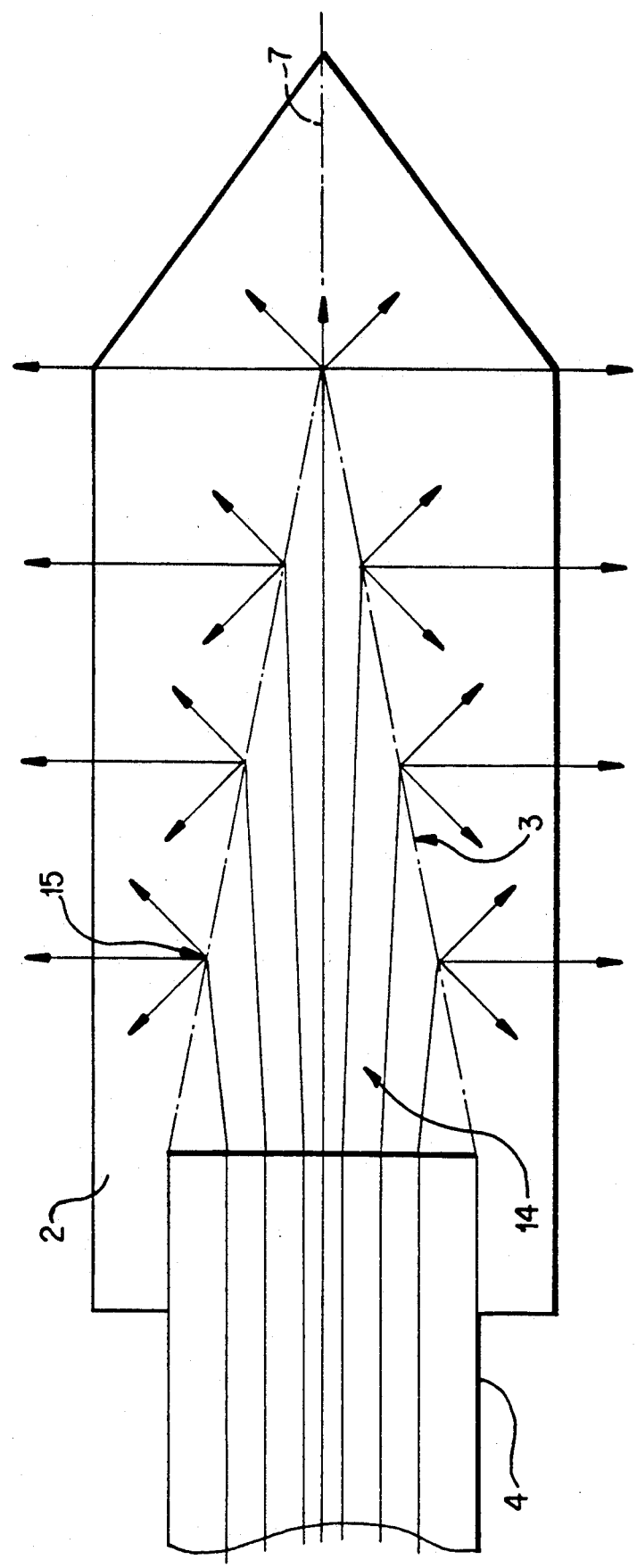
FIG. 2 is a cross sectional view of a fiber optic cylindrical diffuser showing the ray path within, and emitting from, the diffuser.

The cylindrical diffuser 1 has an approximately uniform light output in an outwardly dispersing cylindrical pattern with respect to the central axis 7 of the fiber 4. Referring to FIG. 2, the ray path of the light emitting from the fiber is shown. Light emerging from the end of the flat cut fiber 4 diverges from the central axis 7 because of the change in the index of refraction between the glass of the fiber 4 and the medium inside the tapered central lumen 14. These diverging rays then impact the inside surface 15 of the tapered lumen 3 at various distances along the length of the lumen. Rays which impact this inside surface are diffused outward to the surface of the cylindrical tip 2 and then into space or into a surrounding media such as tissue. The rate at which these rays impact the inner surface of the lumen 3 and hence the rate of energy deflection as a function of linear distance can be controlled by the shape and length of the tapered lumen 3. Thus, it is possible to obtain an output distribution which is radially and linearly uniform even though the energy distribution is not uniform within the core of the fiber optic 4.

In contrast to the prior art which utilizes diffusing coatings which must be manually applied to the fiber at the time of manufacture and which rely on a single optical interface, the present invention makes use of multiple optical interfaces which improves the ability of the device to convert the forward moving light stream into a radially emitting light stream. The optical interfaces at the end of the fiber 4 with the medium of the central lumen 14 begin to refract the light rays radially to contact the second optical interface at the inside surface of the tapered lumen 3 which completes the radial emission of the light ray in a cylindrical pattern. Since the tapered lumen 3 captures the forward moving ray path and converts it radially, there is no need to strip the end of the fiber optic 4 of its protective sheathing 6 to obtain the cylindrical light pattern.

The optical fiber 4 used is one which is suitable for transmitting light of the desired wavelength. Typically, the optical fiber 4 is a quartz optical fiber comprising a quartz core 8 with a diameter of about 400 microns. The core 8 is covered by a protective jacket comprised of a cladding 5 and a sheathing 6. The cladding material has an index of refraction lower than that of the core material, thereby enabling suitably directed light rays within the core to be reflected through the length of the core. Any known type of optical fiber may be utilized with the cylindrical diffuser of the present invention. This includes optical fibers made with cores of glass, fused silica or a polymer such as acrylate or methacrylate, surrounded by a glass or polymer cladding. It is useful to have the sheathing 6 of such thickness to allow a rolled thread for connecting with the cylinder tip 2. One end of the optical fiber 4 is connected via standard connectors to an appropriate laser source.

The cylindrical tip 2 has a closed end portion 9 and is typically made of a colorless glass or plastic material such as polyethylene, Lexan polycarbonate, polyurathane, teflon or molded epoxy. The colorless material contains a suitable optical scattering media such as titanium dioxide, barium sulfate, powdered synthetic sapphire (aluminum oxide), diamond dust or zirconium oxide dust. The scattering material should have a high scattering coefficient at the wavelength of interest when encapsulated in the housing material. Concentrations of the scattering material should be low, typically less than 5%, in order to induce light scattering without causing excessive light absorption.

The central lumen 3 of the cylinder tip 2 may be formed by drilling or boring the center of the cylinder tip or the entire cylinder tip can be formed with the central lumen intact by injection molding and the like. Optionally, the central lumen 3 can be formed using a high powered laser. One of the distinct advantages of the present invention is that output pattern reproducibility can be achieved using a single part manufactured using highly reproducible methods such as injection molding or laser boring. Such techniques can provide reproducible accuracies to the production of these optical diffusing fibers not attainable with the prior art procedures which involve coating exposed fiber tips or tapered fiber tips. The cylinder tip is bored or molded to a depth 10 of about 3 mm at a diameter corresponding to the diameter of the fiber 4 for insertion and attachment of the fiber. The remaining portion of the central lumen is tapered to the desired length.

The cylinder tip 2 may be connected to the fiber 4 by a threaded connection with the jacket 6 of the fiber 4 or the cylinder tip 2 may be pressure bonded, glued or epoxied to the jacket of the fiber. If the fiber is attached with a threaded connection, the jacket may have a thread rolled onto it by the use of a metal die, or the cylinder tip may be threaded in the initial portion of the central lumen which is then used to roll the thread at the time of installation. A small amount of epoxy or cyanoacrylate may be used to ensure a tight connection. For some embodiments, it is conceivable that the tapered central lumen 3 must be larger at the proximal end than the diameter of the fiber. In such embodiments, it would be possible to fit the fiber with a collet having an inside diameter matching that of the fiber and an outside diameter matching that of the lumen. The fiber may then be inserted into the collet which would then be inserted into the lumen.

Figure 3A:
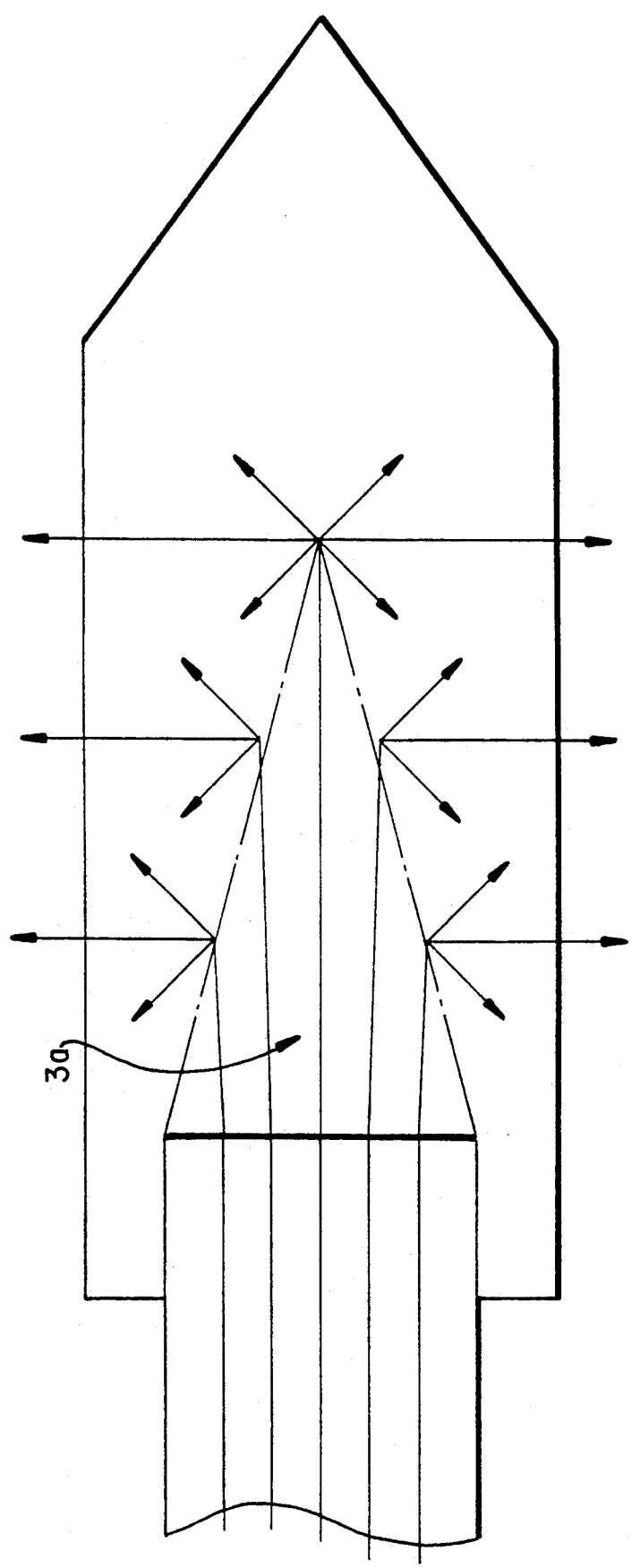
FIG. 3A and 3B show cross-sectional views of two alternative embodiments of the tapered central lumen of the cylindrical diffuser of the present invention.
Figure 3B:
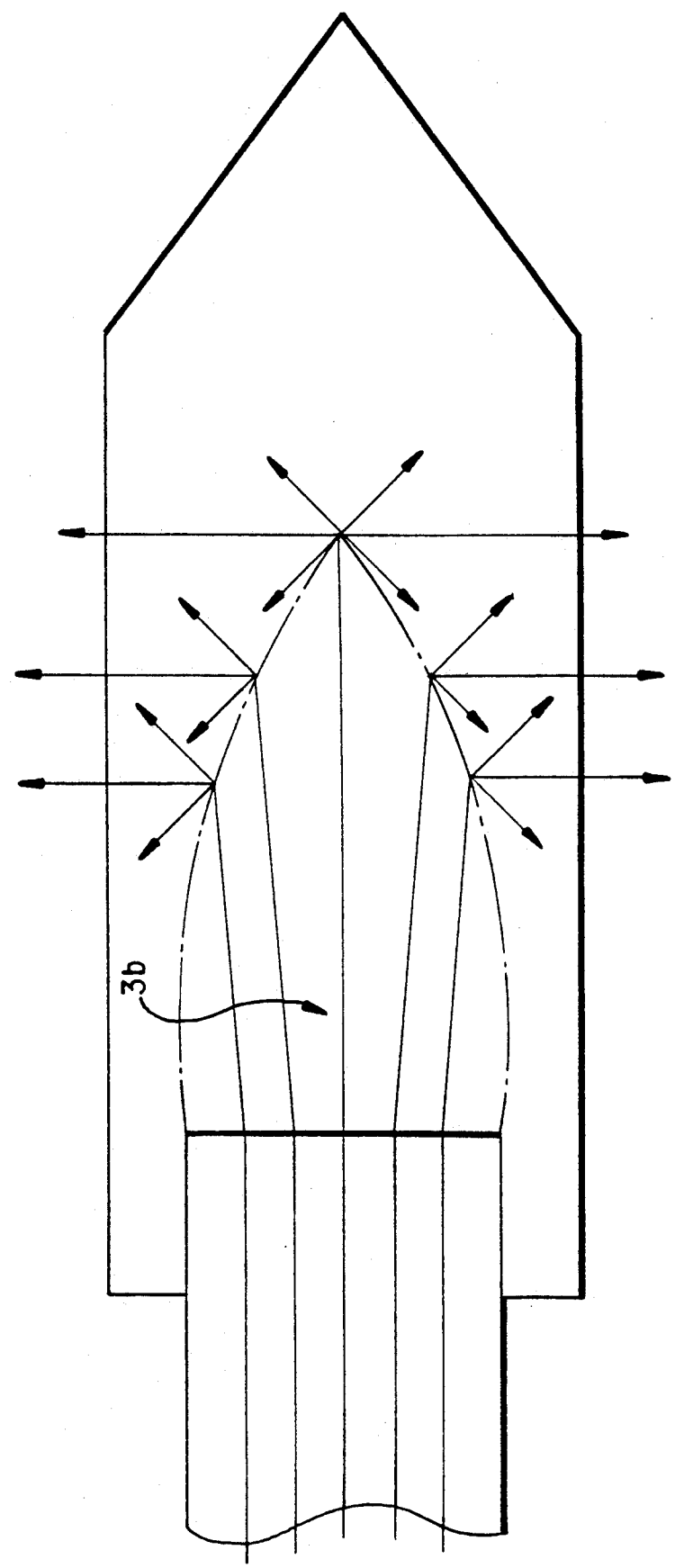

In alternative embodiments, it is possible to purposefully distort or modify the radiation field to provide unique output distributions for specialized applications. As shown in FIGS. 3A and 3B, the configuration of the central lumen 3 may be modified to provide different output distributions of the cylindrical radiation field. FIG. 3A shows the output distribution of a shortened central lumen and FIG. 3B shows the output distribution of a convex shaped lumen 3B. Such modified output distributions may be useful for specialized applications such as use of the diffuser within a catheter system. Such modified devices may be useful within catheters which aid in the access and placement of the fiber optic diffuser within hollow tubes such as the esophagus. In addition, the modified diffuser may be useful in combination with a balloon catheter such as that disclosed in U.S. Pat. No. 5,125,925 for use in the application of photodynamic therapy to body cavities such as the bladder or lung. A distinct advantage of the present invention is the ease with which the output distribution can be modified in manufacture.

The present invention may be used in the treatment of cancer of the esophagus. In application, the optical fiber 4 with the cylindrical diffuser 1 is passed through a flexible tube, catheter or endoscope, such that the cylindrical diffuser is in the region of the tumor sensitized with the photosensitizing drug. Laser light at an appropriate wavelength is introduced into the end of the fiber and light is radiated into the desired cylindrical pattern in the region of the tumor to effect treatment.

It will be understood that various modifications may be employed in connection with the cylindrical diffuser of the present invention without departing from the spirit and scope of the invention.

What is claimed is:

1. A cylindrical fiberoptic diffuser comprising:
   an optical fiber having an end portion for emitting light energy, and
   a cylindrical tip enclosing said end portion,
   said cylindrical tip having a tapered central hollow bore adjacent to the end portion of the optical fiber for emitting the light distribution in a cylindrical pattern.

2. A cylindrical fiberoptic diffuser according to claim 1 wherein the cylindrical tip is comprised of a colorless material containing a scattering medium.

3. A cylindrical fiberoptic diffuser in accordance with claim 2 wherein the colorless material is selected from the group comprised of glass and plastic.

4. The cylindrical fiberoptic diffuser in accordance with claims 2 or 3 wherein the scattering medium is selected from the group comprised of titanium dioxide, barium sulfate, powdered synthetic sapphire, diamond dust and zirconium oxide.

5. A fiberoptic diffuser in accordance with claims 1 or 2 having a substantially uniform light output in a cylindrical radiating pattern with respect to the central axis of the optical fiber.

6. A fiberoptic diffuser in accordance with claim 1 wherein the cylindrical tip has an open end for inserting the optical fiber and a closed end portion, and wherein the tapered central hollow bore has a conical shape which is tapered to an end point adjacent to the closed end portion of the cylindrical tip.

7. A fiberoptic diffuser in accordance with claim 1 wherein said cylindrical tip is in threaded connection with the jacket of the optical fiber.

8. A cylindrical fiberoptic diffuser which is capable of emitting light radiation in a substantially uniform cylindrical scattering pattern and can be used in a biological environment, comprising:
   an optical fiber having an end portion for emitting light energy, and
   a cylindrical tip enclosing said end portion having an open end for inserting the optical fiber and a closed end portion, and a conical shaped, tapered central hollow bore in the cylindrical tip having an open end adjacent to the end portion of the optical fiber and a closed point adjacent to the closed end portion of the cylindrical tip.

9. A method of obtaining controlled light diffusion in a cylindrical pattern from an optical fiber, which comprises; radiating the light from the optical fiber through a central hollow bore of a solid cylindrical tip containing scattering material wherein said bore has a tapered inside surface, in a manner such that the emerging light rays impact the tapered inside surface of the central bore and are diffused radially at a desired angle with respect to the central axis of the optical fiber.

10. A method for manufacture of a cylindrical fiberoptic diffuser, comprising the steps of:
    cleaving the end of optical fiber to obtain a flat end,
    choosing a material which is colorless and transparent to light at a predetermined wavelength and which contains scattering material for diffusing the light in a predetermined manner, and making a desired cylindrical tip with said material, forming a tapered, conical shaped central hollow bore in said cylindrical tip, and
    inserting the flat end of the optical fiber into the central bore of the cylindrical tip and fixing the cylindrical tip to the optical fiber.

* * * * *